United States Patent [19]
Santaniello et al.

[11] Patent Number: 6,051,608

[45] Date of Patent: Apr. 18, 2000

[54] SOLID COMPOSITIONS SUITABLE FOR ORAL ADMINISTRATION COMPRISING L-CARNITINE OR ALKANOYL-L-CARNITINE MAGNESIUM FUMARATE

[75] Inventors: Mosè Santaniello, Nettuno; Nazareno Scafetta, Pavona di Albano; Maria Ornella Tinti, Rome, all of Italy

[73] Assignee: Sigma-Tau Industrie Farmaceutiche Riunite S.p.A., Italy

[21] Appl. No.: 09/402,649

[22] PCT Filed: Apr. 8, 1998

[86] PCT No.: PCT/IT98/00079

§ 371 Date: Oct. 8, 1999

§ 102(e) Date: Oct. 8, 1999

[87] PCT Pub. No.: WO98/49134

PCT Pub. Date: Nov. 5, 1998

[30] Foreign Application Priority Data

Apr. 30, 1997 [IT] Italy .................................. RM97A0254

[51] Int. Cl.$^7$ ........................ A61K 31/205; C07C 229/00
[52] U.S. Cl. ............................................. 514/556; 562/571
[58] Field of Search ............................... 514/556; 562/571

[56] References Cited

FOREIGN PATENT DOCUMENTS

| | | |
|---|---|---|
| 0 402 755 | 12/1990 | European Pat. Off. . |
| 0 434 088 A1 | 6/1991 | European Pat. Off. . |
| 0 628 309 A1 | 12/1994 | European Pat. Off. . |
| 2 529 545 | 1/1984 | France . |
| 1153640 | 5/1969 | United Kingdom . |

*Primary Examiner*—Raymond Henley, III
*Attorney, Agent, or Firm*—Nixon & Vanderhye

[57] ABSTRACT

Stable and non-hygroscopic salts consisting of L-carnitine or alkanoyl-L-carnitine magnesium fumarate are disclosed which are suitable for preparing solid compositions useful as dietary/nutritional supplements for human use and as fodder supplement for veterinary purposes.

11 Claims, No Drawings

SOLID COMPOSITIONS SUITABLE FOR ORAL ADMINISTRATION COMPRISING L-CARNITINE OR ALKANOYL-L-CARNITINE MAGNESIUM FUMARATE

The present invention relates to stable, non-hygroscopic, pharmacologically acceptable salts of L-carnitine and lower alkanoyl-L-carnitines which favourably lend themselves to the preparation of solid, orally administrable compositions, which are useful not only as pharmaceuticals but also for the "health food" and "nutraceutical" market. The present invention also relates to such compositions.

Various therapeutic uses of L-carnitine and alkanoyl derivatives thereof are already known. For instance, L-carnitine has been used in the cardiovascular field for the treatment of acute and chronic myocardial ischaemia, angina pectoris, heart failure and cardiac arrhythmias.

In the nephrological field, L-carnitine has been administered to chronic uraemics undergoing regular haemodialytic treatment to combat myasthenia and the onset of muscular cramps.

Other therapeutic uses relate to the normalization of the HDL:LDL+VLDL ratio and total parenteral nutrition.

As regards the alkanoyl-L-carnitines, acetyl-L-carnitine has been used for the treatment of pathological disturbances of the CNS, particularly Alzheimer's disease and diabetic neuropathy; propionyl-L-carnitine has been used for treating peripheral vascular diseases and congestive heart failure.

It is also known that the salts of L(-)-carnitine and its alkanoyl derivatives present the same therapeutic or nutritional activities as those of the so-called inner salts and can, therefore, be used in their place, provided these salts are "pharmacologically acceptable", i.e. they do not present unwanted toxic or side effects.

In practice, then, the choice between an "inner salt" and a true L(-)-carnitine or alkanoyl-L(-)-carnitine salt will depend essentially on availability, economical and pharmacy considerations rather than on therapeutic or nutritional considerations.

The object of the present invention is to provide stable and non-hygroscopic salts of L-carnitine and lower alkanoyl-L-carnitines which are endowed with an enhanced therapeutical and/or nutritional efficacy with respect to their inner salt counterparts.

It should, therefore, be clearly understood that the utility of the salts of the present invention is not confined to their lack of hygroscopicity and higher stability compared to the corresponding inner salts, but also resides in their enhanced therapeutic and/or nutritional value. This value is, therefore, no longer to be attributed exclusively to the "carnitine" or "alkanoyl-L-carnitine" moiety of the salt. Therefore, although their lack of hygroscopicity allows these salts to be easily compounded, particularly with a view of preparing solid, orally administrable compositions, these salts are inherently useful also as "health foods" or "nutraceuticals".

As is well known to experts in pharmacy, the processing of hygroscopic products entails the use of controlled-humidity chambers both for storage and for the processing itself.

Moreover, the finished products must be packed in hermetically sealed blisters in order to avoid unpleasant consequences due to humidity.

All this involves extra costs both for the storage of raw materials and for their processing and packaging.

Among the populations of the industrialised countries there is an increasingly widespread use of nutritional or dietary supplements, "health foods" or "nutraceuticals" both by sportsmen (amateurs or professionals) and by people in good health.

The former use L-carnitine or nutritional/dietary supplements containing L-carnitine because it facilitates the oxidation of fatty acids and makes a larger amount of energy available to skeletal muscle, thus allowing enhanced performance and giving rise to less accumulation of lactic acid in the athletes' muscles.

People in good health use these nutritional supplements as health foods, i.e. for the purposes of favouring a reduction in serum fat levels and normalisation of the ratio between the various cholesterol fractions in order to prevent diseases related to lipid metabolism disorders.

It has been estimated that the amount of L-carnitine and its derivatives sold for non-ethical purposes is twice that sold for ethical purposes.

The US market for food supplements or nutraceuticals amounts to approximately 250 billion dollars, whereas the estimated figure for the European market is approximately 500 billion dollars (Food Labeling News, 1994, "Nutraceuticals" Market said to be a vast one, March, Vol. 2, n° 25; King Communications Group Inc., 1993, "Nutraceuticals" Foods, Drink in Global Market, Food and Drink Daily, April, Vol. 3, n° 503).

Some non-hygroscopic salts of L-carnitine are already known.

For instance EP 0 434 088 (LONZA) filed Dec. 21, 1990 discloses the use of the non-hygroscopic L(-)carnitine L(+) tartrare (2:1) (the preparation and physico-chemical characterization of which were, however, described by D. Müller and E. Strack in Hoppe Seyler's Z. Physiol. Chem 353, 618–622, April 1972) for the preparation of solid forms suitable for oral administration.

This salt presents, however, some drawbacks, such as e.g. the release, after prolonged storage, of traces of trimethylamine which give the product an unpleasant fishy odour. Moreover, L(-)-carnitine L(+)-tartrate (2:1) becomes deliquescent at relative humidity slightly exceeding 60%. Furthermore, L-(+)-tartaric acid is unable to give non-hygroscopic salts with the alkanoyl-L-carnitines, such as e.g. acetyl-L-carnitine. It should, furthermore, be noticed that tartaric anion is unable by itself to enhance the therapeutic/nutritional value of L-carnitine.

U.S. Pat. No. 4,602,039 (SIGMA-TAU) discloses the acid fumarate of L-carnitine, acetyl-L-carnitine and propionyl-L-carnitine. While the acid fumarate of L-carnitine is strongly non-hygroscopic and withstands even higher values of relative humidity than L-carnitine tartrate does, this ability seems to decline as the weight of the alkanoyl group linked to the L-carnitine backbone increases.

The aforesaid object of the present invention, i.e. to provide novel, pharmacologically acceptable salts of both L-carnitine and lower alkanoyl-L-carnitines which not only are stable and non-hygroscopic but also possess a higher therapeutic and/or nutritional value than the corresponding inner salts, is achieved by the salts of formula (I):

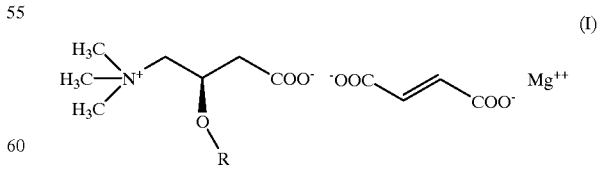

wherein R is hydrogen or a straight or branched lower alkanoyl having 2–5 carbon atoms.

The preferred salts are those wherein R is selected from the group comprising acetyl, propionyl, butyryl, valeryl and isovaleryl.

Since both magnesium and L-carnitine are eliminated in massive amounts with the sweat and urine during prolonged, intense physical activity, the compounds of the present invention can be used to advantage as food supplements for sportsmen.

Magnesium is an important co-factor of the membrane enzymes involved in muscle contraction.

Disorders of magnesium metabolism are usually associated with a reduction in the total plasma concentration. Abnormally low blood levels of magnesium are associated with cardiovascular, neurological and skeletal muscle disorders deriving from cell contractility and excitability abnormalities.

In physiological conditions, the equilibrium constants of the reactions between $Mg^{++}$ and ATP favour the formation of an $MgATP^{2+}$ complex which is used as a substrate by many cellular ATPases.

Magnesium also affects the properties of various ion channels, many of which are situated in various excitable cells, and thus performs a regulatory function with regard to the influx of other ions such as sodium, calcium and potassium.

Magnesium exerts a protective action on cardiac function. The involvement of magnesium in influencing cardiovascular function has 25 recently received considerable attention, both as a therapeutic agent to minimise disorders of an electrophysiological nature and as an aetiological factor in diseases such as myocardial decompensation and hypertension. Epidemiological studies have revealed that there is a distinct correlation between the incidence of cardiac ischaemia and the calcium:magnesium ratio in the diet and drinking water. Hypomagnesaemia gives rise to muscle cramps and to increased activity of the autonomic system.

The following non-limiting example shows the preparation of a non-hygroscopic salt according to the present invention.

EXAMPLE 1

Preparation of L-carnitine magnesium fumarate (ST 1310)

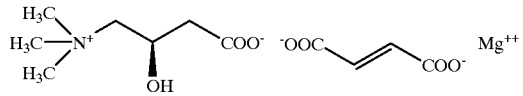

L-carnitine fumarate (5.4 g; 0.02 moles) was dissolved in water and magnesium hydroxide (1.1 g; 0.02 moles) was added to the resulting solution. The mixture was kept under stirring for 2 hours till complete solubilization was achieved.

The solution was concentrated under vacuum at 40° C., the residue taken up with absolute ethanol and the resulting mixture was kept under stirring for 24 hours.

The solution was filtered and a non-hygroscopic solid product (6 g) was obtained.

Thermal analysis:
DSC, the compound decomposes at 170° C. without melting.
Elementary analysis for $C_{11}H_{17}NO_7Mg$
|  | C % | H % | N % |
| --- | --- | --- | --- |
| Calculated (with 8.8% $H_2O$): | 40.3 | 6.2 | 4.2 |
| Found: | 40.5 | 6.6 | 4.1 |

$[\alpha]_D^{25} = -12.09$ (c = 1%, $H_2O$)
NMR $D_2O$ δ 6.5(2H, s, CH=CH); 4.5(1H, m, C̲HOH); 3.4(2H, d, $^+$NC$H_2$); 3.2(9H, s, $(CH_3)_3{}^+N$); 2.4(2H, d, C̲$H_2$COOH)
HPLC:
| Column: | Inertsil-ODS3 (5 μm) 250 × 4.6 mm |
| --- | --- |
| t: | 30° C |
| Eluant:. | $NaClO_4$ 0.15 M + $NaH_2PO_4$ 0.05M |
| pH: | 2.0 with $H_3PO_4$ |
| Carnitine: | $R_t$ = 5.0 min |
| Fumaric acid: | $R_t$ = 11.1 min |
| Mg determination |  |
| Column: | Dionex CG 12 A + CS 12 A 8 μm 4.0 × 250 mm |
| t: | room temperature |
| Eluant: | HCl 25 mN |
| Flow-rate: | 1 mL/min |
| Mg: | $R_t$ = 6.11 min |

EXAMPLE 2

Preparation of acetyl L-carnitine magnesium fumarate (ST 1311)

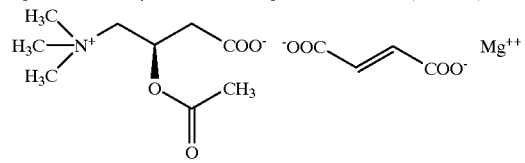

Acetyl L-carnitine inner salt (4.1 g; 0.02 moli), fumaric acid (2.3 g; 0.02 moles) and magnesium hydroxide (1.1 g; 0.02 moles) were suspended in 100 mL of $H_2O$ and the resulting mixture was kept under stirring for about 2 hours till complete solubilization was achieved. The solution was then concentrated under vacuum at 40° C.

The residue was taken up with absolute ethanol at 40° C. and the resulting mixture was kept under stirring for about 2 hours. The mixture was then filtered and 6.3 g of a solid, non-hygroscopic compound were obtained.

Thermal anaylsis:
DSC, the compound decomposes at 160° C. without melting.
Elementary anaylsis for $C_{13}H_{19}NO_8Mg$
|  | C % | H % | N % |
| --- | --- | --- | --- |
| Calculated (with 11.7% $H_2O$): | 40.3 | 6.2 | 3.1 |
| Found: | 38.8 | 5.9 | 2.9 |

$[\alpha]_D^{25} = -11.9$ (c = 1%, $H_2O$)
NMR $D_2O$ δ 6.5(2H, s, CH=CH); 5.5(1H, m, C̲HOH); 3.9–3.5(2H, m, $^+$NC$H_2$); 3.1(9H, s, $(CH_3)_3{}^+N$); 2.6–2.3(2H, m, C̲$H_2$COOH); 2.1(3H, s, $COCH_3$).
HPLC: as described for ST 1310
| Acetyl-L-carnitine: | $R_t$ = 19.8 min |
| --- | --- |
| Fumaric acid: | $R_t$ = 11.1 min |
| Mg: | $R_t$ = 6.11 min |

The present invention also relates to compositions comprising as active principle(s) at least one of the aforesaid non-hygroscopic pharmacologically acceptable salts and, optionally, one or more pharmacologically acceptable excipients and active ingredients which are well-known to the experts in pharmacy and food technology.

Particularly preferred are the solid, orally administrable compositions such as tablets, chewable tablets and capsules, which comprise a salt of L-carnitine or alkanoyl-L-carnitine of formula (I) in an amount corresponding to 50–2,000 mg, preferably 100–1,000 mg, of L-carnitine or alkanoyl-L-carnitine inner salt.

For instance, a composition for preparing tablets is the following:

| | |
|---|---|
| Non-hygroscopic L-carnitine salt of formula (I) | 500 mg |
| Starch | 20 mg |
| Talc | 10 mg |
| Calcium stearate | 1 mg |
| | 531 mg |

A composition suitable for preparing capsules is the following:

| | |
|---|---|
| Non-hydroscopic L-carnitine salt of formula (I) | 500 mg |
| Starch | 20 mg |
| Lactose | 50 mg |
| Talc | 5 mg |
| Calcium stearate | 2 mg |
| | 577 mg |

The compositions of the present invention may be used as dietary/nutritional supplements for human use or as fodder supplement for veterinary purposes.

Through the synergic action exerted by the component moieties of the present salts, the following results are achieved:

enhanced enzymatic activity bound to the energy metabolism;

improved endurance and adaptation to programs of strenous exercise with achievement of higher performances and shorter rest periods;

strengthening of the functional capacity of the cardiovascular system; and less tendency to develop muscular cramps.

What is claimed is:

1. A salt of L-carnitine or alkanoyl-L-carnitine of formula (I)

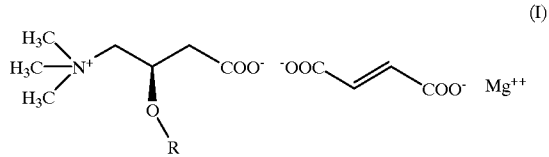

wherein R is hydrogen or a straight or branched lower alkanoyl having 2–5 carbon atoms.

2. The salt of claim 1, wherein R is selected from the group comprising acetyl, propionyl, butyryl, valeryl and isovaleryl.

3. L-carnitine magnesium fumarate.

4. Acetyl-L-carnitine magnesium fumarate.

5. Propionyl-L-carnitine magnesium fumarate.

6. A composition comprising as active ingredient a salt according to claim 1.

7. The composition of claim 6, further comprising one or more substances selected from pharmacologically acceptable excipients and active ingredients.

8. The composition of claim 6, in the form of tablets, chewable tablets, capsules, granulates or powders.

9. The composition of claim 6, in unit dosage form comprising as active ingredient a salt of L-carnitine or alkanoyl-L-carnitine of formula (I), in an amount corresponding to 50–2,000 mg, preferably 100–1,000 mg, of alkanoyl-L-carnitine inner salt.

10. The composition of claim 6 as dietary/nutritional supplement for human use.

11. The composition of claim 6 as fodder supplement for veterinary use.

* * * * *